United States Patent [19]

Higuchi et al.

[11] Patent Number: 4,462,991

[45] Date of Patent: Jul. 31, 1984

[54] METHOD OF INCREASING ORAL ABSORPTION OF POLAR BIOACTIVE AGENTS

[75] Inventors: Takeru Higuchi; Toshiaki Nishihata, both of Lawrence, Kans.

[73] Assignee: INTERx Research Corp., Lawrence, Kans.

[21] Appl. No.: 387,410

[22] Filed: Jun. 11, 1982

Related U.S. Application Data

[63] Continuation-in-part of Ser. No. 213,124, Dec. 5, 1980, abandoned, which is a continuation-in-part of Ser. No. 128,101, Mar. 7, 1980, abandoned.

[51] Int. Cl.$^3$ .............................................. A61K 37/02
[52] U.S. Cl. ..................................... 424/177; 424/230; 424/231; 424/232; 424/233; 424/234; 424/235
[58] Field of Search ............................... 424/230–235, 424/177

[56] References Cited

FOREIGN PATENT DOCUMENTS 2258171 8/1975 France .

OTHER PUBLICATIONS

Gibaldi, M., et al., *J. Pharm. Sci.*, 62(2), 343–344 (1973).
Imamura, Y., et al., *Chem. Pharm. Bull.*, (Japan), 22, 2324–2328 (1974).
Spector, R., et al., *J. Pharm. Exp. Ther.*, 188(1), 55–65 (1974).
Corell, T., et al., *Acta Pharmacol. et Toxicol.*, 45, 225–231 (1979).
Samejima, M., et al., *Yakugaku Zasshi*, 88(5), 618–622 (1968).
Sugimoto, I., et al., *Yakugaku Zasshi*, 88(6), 690–694 (1968).

*Primary Examiner*—Richard A. Schwartz
*Attorney, Agent, or Firm*—Manfred Polk; Michael C. Sudol, Jr.

[57] ABSTRACT

A method and drug form are provided for increasing the oral absorption of polar bioactive agents such as polypeptides by the oral administration of said polar bioactive agents in a suitable pharmaceutically accepted excipient to which has been added a hydroxyaromatic acid or salt as an adjuvant thereof. The adjuvant is present in the drug form in quantities sufficient to be effective in enhancing the rate of oral absorption of the polar bioactive agents.

10 Claims, No Drawings

METHOD OF INCREASING ORAL ABSORPTION OF POLAR BIOACTIVE AGENTS

CROSS-REFERENCE TO RELATED APPLICATIONS

This application is a continuation-in-part of our previous application Ser. No. 213,124 filed in the U.S. Patent & Trademark Office on Dec. 5, 1980 entitled "Method of Increasing Oral Absorption of Polar Bioactive Agents", now abandoned, is a continuation-in-part of our previous application Ser. No. 128,101 filed Mar. 7, 1980 in the U.S. Patent and Trademark Office, entitled "Method of Increasing Oral Absorption of Polar Bioactive Agents", now abandoned.

BACKGROUND OF THE INVENTION

1. Field of the Invention

The present invention relates to the oral delivery of polar bioactive agents particularly polypeptides which by this route are slowly absorbed and more especially to the enhancement of this delivery by formulations which contain a hydroxyaromatic acid.

As employed in this application, the term "polar bioactive agents" refers to those therapeutic substances which, due to their polar nature, are slowly absorbed from the gastrointestinal tract and include particularly, polypeptides which have three or more residues of amino acids with a molecular weight of 4000 or less.

2. Description of the Prior Art

It is well known to the art that a number of bioactive agents are so polar that they are only slowly absorbed from the gastrointestinal tract. Consequently, these agents, on the basis of the current art, must be administered by the intravenous or intramuscular route or in excessively large oral doses in order to attain clinical efficacy. Similarly, there are a number of other polar bioactive agents such as the polypeptides which, due to their hydrophilic nature, are also slowly absorbed from the gastrointestinal tract. The hydrophilic, polar nature of these agents precludes their rapid absorption so that even the small percentage which is absorbed is subject to a long residency time in the gastrointestinal environment where both acidic and enzymatic degradation contribute to their poor bioavailability. It is therefore clear that any factor which enhances the rate of absorption will demonstrate improved clinical efficacy.

Many attempts have been made to improve the oral absorption of these polar bioactive agents. The degradation caused by the gastric acid and enzymes can be partially overcome by coating. This process in some instances can lead to some enhanced oral absorption, but in no case does it allow complete absorption. Other approaches center on the reduction of the hydrophilicity by preparing a chemical derivative which is more lipophilic. The more lipophilic derivative is more rapidly absorbed so that the residency time in the degrading gastric medium is minimized.

In spite of the numerous attempts to prepare a dosage form of these polar bioactive agents, there still exists a clear and present need for a novel method to enhance the oral absorption of polar bioactive agents, particularly polypeptides. Said method would permit the oral use of a number of polypeptides, and would provide an improved oral dosage form for such polypeptides.

SUMMARY OF THE INVENTION

Accordingly, a major object of this invention is to provide a class of agents or adjuvants which enhance the oral absorption of polypeptides (polar bioactive agents).

Another object is to provide a process utilizing said class of agents to enhance the oral absorption of polypeptides.

Another object is to provide a stable drug form utilizing said class of agents which when administered orally will provide increased blood levels of the therapeutic agent.

Other objects, features and advantages of the invention will be apparent to those skilled in the art from the detailed description of the invention which follows.

All of the foregoing objects are readily attained by providing a method and drug form wherein the oral absorption of polar bioactive agents, particularly polypeptides, is enhanced, the method comprising the steps of preparing a drug form suitable for oral delivery, and a drug form comprising an effective unit dosage amount of the polypeptide drug agents, a hydroxyaromatic acid or salt thereof, the latter adjuvants being present in said drug form in an amount sufficient to be effective in enhancing the rate of the oral absorption of the therapeutic substance, and a suitable pharmaceutically acceptable excipient.

DETAILED DESCRIPTION OF THE INVENTION

The present invention, generally comprises the steps of preparing a drug form capable of being orally administered, wherein the drug form comprises an effective unit dosage amount of a polypeptide drug and a hydroxyaromatic acid or salt thereof, the hydroxyaromatic acid or salt thereof being present in the drug form in a sufficient quantity to be effective in enhancing the oral absorption rate and administering the drug form to warm-blooded animals. The amount of polypeptide varies over a wide range, but generally any therapeutically effective unit dosage amount of the selected polypeptide is used.

The hydroxyaromatic acids or their salts thereof that are used as the adjuvants in our method and in our drug forms have the following structural formulae including the various isomers possible within the formulae set forth:

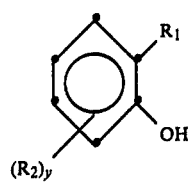

Formula I wherein $R_1$ is $CO_2H$, $-(CH_2)-COOH$,

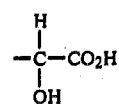

$SO_3H$, or a pharmaceutically acceptable salt thereof such as the sodium salt or the calcium salt wherein $R_2$ is OH, H, a lower alkoxy radical including methoxy, ethoxy, butoxy, or octyloxy, a lower alkyl radical including methyl, isopropyl, ethyl, t-butyl, n-butyl, or t-octyl, a halo radical, or a tri-halo lower alkyl radical including trifluoromethyl, and wherein y is an integer of 1 or 2.

More preferred adjuvants of Formula I are those compounds wherein the $R_1$ and OH groupings are ortho to each other.

Specific adjuvants useful in our method and drug forms for enhancing oral absorption of the polypeptide agents include the following:
1. Sodium salicylate
2. Sodium-5-methoxysalicylate
3. Sodium-5-chlorosalicylate
4. Sodium-5-bromosalicylate
5. 5-trifluorosalicylic acid
6. 3-t-butyl-5-methylsalicylic acid
7. Sodium-5-t-octylsalicylate
8. Sodium-3,5-diiodosalicylate
9. 5-n-butyoxysalicylic acid or
10. 3-t-butyl-6-methylsalicylic acid Such adjuvants are not considered novel per se and may be prepared by techniques known to those skilled in the art.

The amount of adjuvant of Formula I used in our method and drug forms may vary over a wide range; in general, the identity and the amount of the adjuvant used in connection with the drug is such to be effective in enhancing the absorption rate of the drug from the gastrointestinal compartment into the bloodstream. Generally the amount of adjuvant used per unit dosage of the particular drug being administered is in the range of 50 mg to 750 mg. The amount of adjuvant to be effective will vary depending on the particular drug used and the release characteristics of the particular dosage form used. (For example, a rapidly disintegrating drug delivery device or a slow release device will have different adjuvant requirements.) The effectiveness of the adjuvants becomes significant at local concentration exceeding 0.01% at the absorption site. Their use at a dosage whereby their concentration at the absorption site exceeds 5% is not recommended because of the local irritating effect on the tissue.

The polypeptide agents whose enhanced oral delivery is a subject of the present invention encompasses polypeptides having three (3) or more residues of amino acids and having a molecular weight of 4000 or less. Examples of polypeptides which fall within the above parameters are the following:
bradykinin
somatostatin
calcitonin
endorphin
secretin
oxytocin
T.S.H. (thyrotropin) or
Cyclo-(N-Me-Ala-Tyr-D-Trp-Lys-Val-Phe)

The quantity of these polypeptide agents necessary for preparing the drug form could vary over a wide range, but would normally be regulated by that quantity necessary to comprise the therapeutically effective dosage form.

The drug forms of this invention are suitably administered in oral dosage form, such as by tablet or capsule, by combining the polypeptide agent in a therapeutic amount and the adjuvant of Formula I in a sufficient quantity to be effective to enhance oral delivery with an oral pharmaceutically acceptable inert carrier, such as lactose, starch (pharmaceutical grade), dicalcium phosphate, calcium sulfate, Kaolin, mannitol and powdered sugar. In order to reduce the irritation in the stomach, the preferred dose form of the adjuvant of Formula I should be a pharmaceutically acceptable salt and the drug form should be designed to release the polypeptide agent and the hydroxyaromatic acid salt beyond the pylorus. In addition, when required, suitable binders, lubricants, disintegrating agents, and coloring agents can also be added. Typical binders include, without limitation, starch, gelatin, sugars such as sucrose, molasses, and lactose, natural and synthetic gums, such as acacia, sodium alginate, extract of Irish moss, carboxymethylcellulose, methylcellulose, and polyvinylpyrrolidone, polyethylene glycol, ethylcellulose and waxes. Typical lubricants for use in these dosage forms can include, without limitation, boric acid, sodium benzoate, sodium acetate, sodium chloride, leucine and polyethylene glycol. Suitable disintegrators can include, without limitation, starch, methylcellulose, agar, bentonite, cellulose and wood products, alginic acid, guar gum, citris pulp, carboxymethylcellulose, and sodium lauryl sulfate. Optionally, if desired, a conventionally, pharmaceutically acceptable dye can be incorporated into oral dosage unit form, e.g., any of the standard FD & C dyes.

EXAMPLE I

Typical preparation of enteric-coated tablets containing adjuvant.

| 125 mg Polypeptide Tablets Ingredient | Amount per Tablet |
| --- | --- |
| Cyclo-(N—Me—Ala—Tyr—D-Trp—Lys—Val—Phe) | 125 mg |
| Sodium 5-methoxysalicylate | 250 mg |
| Microcrystalline cellulose | 150 mg |
| Lactose | 95 mg |
| Magnesium stearate | 40 mg |
| | Total 660 mg |

All ingredients except ¼ of the magnesium stearate were mixed and the material slugged using ½" flat head punches. The slugs were broken up and passed through a 40 mesh screen. The remaining magnesium stearate was added and mixed in. Tablets were made with 7/16" deep concave punches to a hardness of 10 Kg.

Coating:

The tablets were coated with 11 mg of pre-coat and 32 mg of enteric coating according to the coating procedure described below.

Enteric Coating Procedure

Tablets or capsules were placed in a coating pan containing baffles to provide adequate tumbling. A small amount of the coating solution was applied using an air sprayer and the solvents evaporated with a warm air supply directed into the coating pan. This procedure was repeated until the desired amount of coating material was applied. The amount of coating material was determined from the weight gain of a representative group of tablets.

Coating Solutions:

Pre-coat: A film of hydroxypropylmethylcellulose was applied to the tablets followed by an enteric coating.

Enteric coat: A film of hydroxypropylmethyl- cellulosephthalate was applied.

Solutions: A 5% by weight solution of hydroxypropylmethylcellulose and a 10% by weight solution of hydroxypropylmethylcellulosephthalate in ethanol:-methylene chloride (1:1 by weight) were used as the coating solutions.

EXAMPLE II

The following tests were run showing Percent Bioavailability (% BA)

| Drug | Control | Adjuvant 1 | 2 |
|---|---|---|---|
| Cyclo-(N—Me—Ala—Tyr—D-Trp—Lys—Val—Phe) | 1% BA | 7% BA | 20% BA |

Adjuvant 1 is Sodium salicylate
Adjuvant 2 is Sodium-5-methoxy salicylate

The above tests were done according to the following protocol:

| Animals: | Male Sprague-Dawley rats (200-250 g) |
|---|---|
| Anesthesia: | Ethyl carbamate by i.m. injection |
| Blood sampling: | 0.6 ml from external jugular vein at 15, 30, 60 and 90 minutes. $(AUC)_0^{90}$ calculated from summation of trapezoid areas |
| Bioavailability: | % Bioavailability = $\frac{(AUC)\text{rectal (Dose)i.v.}}{(AUC)\text{i.v. (Dose)rectal}} \times 100$ |

For the oral test an intraduodenal injection 1.0 cm distal to the pylorus was done. The volume of the injection was 0.25 ml at 0.3 ionic strength (adjusted with sodium chloride) and a pH of 5.

The drug was administered at 10 mg/ml unless otherwise noted and the adjuvant at 20 mg/ml unless otherwise noted.

The (AUC)i.v. was determined for each drug, based on the mean value from 3-6 animals.

Any skilled artisan concerned with the subject matter of this invention can prepare these oral dosage forms by simply referring to the oral dosage form preparatory procedure outlined in REMINGTON'S PHARMACEUTICAL SCIENCES, Fifteenth Edition (1975), pages 1576 through 1617 inclusive.

From the foregoing description, one of ordinary skill in the art can easily ascertain the essential characteristics of this invention, and without departing from the spirit and scope thereof, can make various changes and modifications of the invention to adapt it to varius usages and conditions. As such, such changes and modifications are properly, equitably, and intended to be, within the full range of equivalence of the following claims.

What is claimed is:

1. A method for enhancing the rate of absorption of an orally administeredpolypeptide drug having 3 or more residues of amino acid and having a molecular weight of 4000 or less into the bloodstream, said method comprising the steps of preparing a drug form capable of being orally absorbed, said drug form comprising a therapeutically effective dosage amount of said polypeptide drug and an adjuvant of the formula:

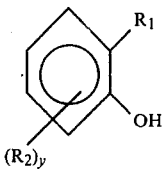

wherein $R_1$ is $CO_2H$, $-(CH_2)-COOH$, $$-\overset{\overset{\displaystyle H}{|}}{\underset{\underset{\displaystyle OH}{|}}{C}}-CO_2H,$$

$SO_3H$, or a pharmaceutically acceptable salt thereof wherein $R_2$ is OH, H, a lower alkoxy radical, a lower alkyl radical, a halo radical, or a tri-halo lower alkyl radical, and wherein y is an integer of 1 or 2; said adjuvant being present in said drug form in a sufficient amount to be effective in enhancing said oral absorption rate and administering said drug form orally to a warm blooded animal.

2. The method of claim 1 wherein said polypeptide drug is bradykinin, somatostatin, calcitonin, endorphin, secretin, oxytocin, TSH or Cyclo-(N-Me-Ala-Tyr-D-Trp-Lys-Val-Phe).

3. The method of claim 2 wherein said polypeptide drug is Cyclo-(N-Me-Ala-Tyr-D-Trp-Lys-Val-Phe).

4. The method of claim 1 wherein said adjuvant is sodium salicylate, sodium 5-methoxysalicylate, sodium-5-chlorosalicylate, sodium-5-bromosalicylate, 5-trifluorosalicylic acid, 3-t-butyl-5-methylsalicylic acid, sodium-5-t-octylsalicylate, sodium-3,5-diiodosalicylate, 5-n-butyoxysalicylic acid, or, 3-t-butyl-6-methylsalicylic acid.

5. The method of claim 1 wherein the adjuvant is salicylic acid, sodium salicylate, or sodium-5-methoxy salicylate.

6. An orally administered drug form comprising a therapeutically effective amount of a polypeptide drug having 3 or more residues of amino acids and having a molecular weight of 4000 or less and an adjuvant of the Formula

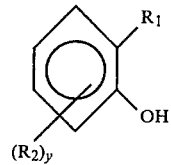

wherein $R_1$ is $CO_2H$, $-(CH_2)-COOH$, $$-\overset{\overset{\displaystyle H}{|}}{\underset{\underset{\displaystyle OH}{|}}{C}}-CO_2H,$$

or
$SO_3H$, or a pharmaceutically acceptable sodium or calcium salt thereof wherein $R_2$ is OH, H, lower alkoxy radical, a lower alkyl radical, a halo radical, or a tri-halo lower alkyl radical, and wherein y is an integer of 1 or 2;

said adjuvant being present in said drug form in sufficient amount to be effective in enhancing the oral absorption rate of said polar bioactive agent.

7. The drug form of claim 6 wherein the said polypeptide drug is bradykinin, somatostatin, calcitonin, endorphin, secretin, oxytocin, TSH or Cyclo-(N-Me-Ala-Tyr-D-Trp-Lys-Val-Phe).

8. The drug form of claim 6 wherein said polypeptide is Cyclo-(N-Me-Ala-Tyr-D-Trp-Lys-Val-Phe).

9. The drug form of claim 6 wherein said adjuvant is sodium salicylate, sodium 5-methoxysalicylate, sodium-5-chlorosalicylate, sodium-5-bromosalicylate, 5-trifluorosalicylic acid, 3-t-butyl-5-methylsalicylic acid, sodium-5-t-octylsalicylate, sodium-3,5-diiodosalicylate, 5-n-butyoxysalicylic acid, or, 3-t-butyl-6-methylsalicylic acid.

10. The drug form of claim 6 wherein the adjuvant is salicylic acid, sodium salicylate or sodium-5-methoxy salicylate.

* * * * *